United States Patent
Lippmann

[11] 3,937,801
[45] Feb. 10, 1976

[54] REDUCING THE INCIDENCE OF GASTROINTESTINAL SIDE EFFECTS DURING THE TREATMENT OF INFLAMMATORY CONDITIONS WITH ANTIINFLAMMATORY DRUGS

[75] Inventor: Wilbur Lippmann, Montreal, Canada

[73] Assignee: American Home Products Corporation, New York, N.Y.

[22] Filed: July 10, 1973

[21] Appl. No.: 378,112

[52] U.S. Cl. .................. 424/10; 424/234; 424/273; 424/274; 424/305; 424/317
[51] Int. Cl.² .................. A61K 31/19; A61K 31/40; A61K 31/61
[58] Field of Search ............ 424/305, 318, 10, 234, 424/274, 273, 317

[56] References Cited
OTHER PUBLICATIONS
Lippmann – Chem. Abst., Vol. 75, (1971), p. 59247n.

Primary Examiner—Sam Rosen

[57] ABSTRACT

A method is disclosed for inhibiting and alleviating gastrointestinal side effects often encountered during therapy with antiinflammatory agents such as indomethacin, phenylbutazone, oxyphenylbutazone and the like. The method comprises the administration to a mammal receiving such therapy of a prostaglandin derivative of formula 1,

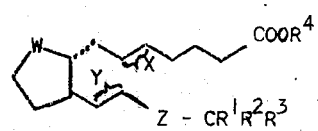

in which
a. W is $C=O$, X and Y each are single bonds, Z is either $C=O$, CHOH or $C(CH_3)OH$, $R^1$ and $R^2$ each are hydrogen, $R^3$ is $(CH_2)_3CH_3$ and $R^4$ is hydrogen or lower alkyl;
b. W is CHOH, X and Y each are single bonds, Z is either CHOH or $C(CH_3)OH$, $R^1$ and $R^2$ each are hydrogen, $R^3$ is $(CH_2)_3CH_3$ and $R^4$ is hydrogen or lower alkyl;
c. W is $C=O$, X is a single bond, Y is a trans double bond, Z is $CH_2$, CHOH or $C(CH_3)OH$, $R^1$ and $R^2$ each are hydrogen and $R^3$ is $(CH_2)_3CH_3$ and $R^4$ is hydrogen or lower alkyl;
d. W is $C=O$, X is a single bond, Y is a trans double bond, Z is CHOH, $R^1$ and $R^2$ each are hydrogen, $R^3$ is cyclohexyl and $R^4$ is hydrogen or lower alkyl;
e. W is $C=O$, X is a cis double bond, Y is a trans double bond, Z is CHOH, or $C(CH_3)OH$, $R^1$ is hydrogen and $R^2$ is hydrogen or methyl, $R^3$ is $(CH_2)_3CH_3$ and $R^4$ is hydrogen or lower alkyl; or
f. W is $C=O$, X is a cis double bond, Y is a trans double bond, Z is CHOH, $R^1$ and $R^2$ each are methyl, $R^3$ is $(CH_2)_3CH_3$ and $R^4$ is hydrogen or lower alkyl.

Also disclosed are useful pharmaceutical compositions for treating inflammatory conditions comprising a combination of a gastrointestinal side effect-inhibiting dose of the above prostaglandin derivative of formula 1 and a therapeutic dose of an antiinflammatory agent.

2 Claims, No Drawings

REDUCING THE INCIDENCE OF GASTROINTESTINAL SIDE EFFECTS DURING THE TREATMENT OF INFLAMMATORY CONDITIONS WITH ANTIINFLAMMATORY DRUGS

BACKGROUND OF THE INVENTION a. Field of Invention

This invention relates to a method and to compositions for reducing or treating gastrointestinal side effects caused by antiinflammatory agents. More particularly, this invention relates to the finding that the adminstration of certain prostaglandin derivatives to a mammal inhibits and alleviates the gastrointestinal side effects, for example, ulceration, gastrointestinal bleeding, epigastric distress, diarrhea, melena and the like, associated with antiinflammatory drug therapy.

b. Background of the Invention

Antiinflammatory agents, for example, indomethacin, phenylbutazone, oxyphenylbutazone, aspirin and the like, are useful for the treatment of arthritic and rheumatic diseases. However, the use of these agents is associated with a rather high incidence of side effects, the most serious being those related to gastrointestinal reactions. In fact, it has been stated that one of the most common reasons for discontinuing therapy with such agents is the development of a peptic ulcer.

Realizing the serious drawback of this form of therapy, Y. H. Lee, et al., Arch. Int. Pharmacodyn. Ther., 192, 370 (1971), administered various known antiulcer compounds to rats treated with a gastric ulcer-producing dose of indomethacin to evaluate the possible utility of serveral types of antiulcer compounds in reducing the ulcerogenic activity of indomethacin. Some of the compounds evaluated, for example propantheline bromide, proved to be effective but only when administered at does much higher than their usual therapeutic dose.

In a related development it has been suggested that certain prostaglandin derivatives may be of value for the treatment of peptic ulcers. This suggestion is based on the finding that prostaglandin $E_1$ and several of its analogs inhibit gastric acid secretion; for example, see W. Lippmann, Ann. N.Y. Acad. Sci., 180, 332 (1971).

In view of the foregoing the finding of the present disclosure is surprising and interesting indeed. Namely, it has been found that the prostaglandin derivatives of the present disclosure inhibit ulcer formation and alleviate the symptoms concerned therewith at doeses substantially less than those required for the inhibition of the basal secretion of gastric acid.

This finding is even more surprising in light of the finding that similar inhibition and treatment of aspirin-induced ulcers is achieved at doses of prostaglandins substantially more than required for the inhibition of basal secretion of gastric acid.

Furthermore, other gastrointestinal disturbances associated with the antiinflammatory agents as well as the diarrheal effect associated with larger doses of the natural prostaglandins, for example, prostaglandin $E_1$ [J.J. Misiewicz, et al., Lancet, 1, 648 (1969)], are antagonized and minimized.

It is worth noting at this point that the natural $PGE_1$, $PGE_2$, $PGF_{1\alpha}$ and $PGF_{2\alpha}$ do have the disadvantage of being relatively unstable, see T.O. Oesterling, et al., J. Pharm. Sci., 61, 1861 (1972). For example, it is well known that the 11-hydroxy group of $PGE_1$ and $PGE_2$ participates readily in dehydration reactions under both basic and acidic conditions, see S. Bergstrom et. al., J. Biol. Chem. 238, 3555 (1963), E.J. Corey et al., J. Amer. Chem. Soc., 90, 3245 (1968), J.E. Pike et al., J. Org. Chem. 34, 3552 (1969) and "The Prostaglandins, Progress in Research," S.M.M. Karim, Ed., Wiley-Interscience, New York, 1972, p. 10.

As realized by those skilled in the art this inherent disadvantage of the natural compounds must always be taken in account when considering the practical aspects of preparation, formulation or storage of these compounds. In contrast, the compounds of formula 1 are free from this disadvantage.

SUMMARY OF THE INVENTION

According to the method of this invention an effective gastrointestinal side effect-inhibiting amount of the prostaglandin derivative of formula 1,

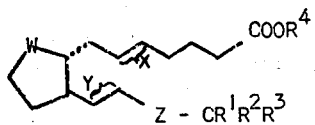

in which a. W is C = O, X and y each are single bonds, Z is either C = O, CHOH or C(CH$_3$) OH, R$^1$ and R$_2$ each are hydrogen, R$^3$ is (CH$_2$)$_3$CH$_3$ and R$^4$ is hydrogen or lower alkyl;

b. W is CHOH, X and Y each are single bonds, Z is either CHOH or C(CH$_3$)OH, R$^1$ and R$^2$ each are hydrogen, R$^3$ is (CH$_2$)$_3$CH$_3$ and R$^4$ is hydrogen or lower alkyl;

c. W is C = O, X is a single bond, Y is a trans double bond, Z is CH$_2$, CHOH or C(CH$_3$)OH, R$^1$ and R$^2$ each are hydrogen and R$^3$ is (CH$_2$)$_3$CH$_3$ and R$^4$ is hydrogen or lower alkyl;

d. W is C = O, X is a single bond, Y is a trans double bond, Z is CHOH, R$^1$ and R$^2$ each are hydrogen, R$^3$ is cyclohexyl and R$^4$ is hydrogen or lower alkyl;

e. W is C = O, X is a cis double bond, Y is a trans double bond, Z is CHOH or C(CH$_3$)OH, R$^1$ is hydrogen and R$^2$ is hydrogen or methyl, R$^3$ is (CH$_2$)$_3$CH$_3$ and R$^4$ is hydrogen or lower alkyl; or f. W is C = O, X is a cis double bond, Y is a trans double bond, Z is CHOH, R$^1$ and R$^2$ each are methyl, R$^3$ is (CH$_2$)$_3$CH$_3$ and R$^4$ is hydrogen or lower alkyl;

is administered to an antiinflammatory agent-treated mammal so that the gastrointestinal side effects induced by the antiinflammatory agent therapy are reduced.

In another aspect of this invention there is disclosed a pharmaceutical composition in unit dosage form for treating inflammatory conditions comprising a combination of a gastrointestinal side effect-inhibiting dose of the prostaglandin derivative of formula 1 and a therapeutic dose of an antiinflammatory agent.

DETAILS OF THE INVENTION

It should be noted that, like the natural prostaglandins, the compounds of formula 1 have two side chains which are in a trans relationship to each other. Also, like the natural prostaglandins, a double bond in the acid side chain of the compounds of this invention has the cis configuration and the double bond in the side chain bearing the hydroxy group has the trans configuration.

Notwithstanding the preceding considerations the compounds of this invention having one or more asymmetric carbon atoms can exist in the form of various stereochemical isomers, i.e. racemates and enantiomorphs. It is to be understood that such racemates and enantiomorphs are included within the scope of this invention.

Furthermore, it is to be understood that the pictorial representation used herein illustrating the compounds of this invention, is to be construed as including such racemates and enantiomorphs. More explicitly, in formula 1 the dotted line joining the acid side chain to the cyclopentane ring and the solid line joining the alkyl or substituted alkyl side chain are used for the purpose of illustrating the trans relationship of these two side chains and should not be construed as limiting the compounds to one enantiomorph but rather as including all possible enantiomorphs having this trans relationship.

The prostaglandin derivatives of this invention in which $R^4$ is hydrogen, i.e. the acid derivatives of formula 1 form pharmaceutically acceptable salts with suitable inorganic and organic bases. These derived salts possess the same activity as the parent acid and are included within the scope of this invention. The acid is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, such as mono-, di- and triethanolamine; alkylene-diamines which contain up to six carbon atoms, such as hexamethylene diamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and n-(2-hydroxyethyl)piperidine, as well as pyridine. Furthermore, there may be mentioned the corresponding quaternary salts, such as the tetraalkyl (for example tetramethyl), alkyl-alkanol (for example methyl-trimethanol and trimethyl-monoethanol) and cyclic ammonium salts, for example the N-methyl-pyridinium, N-methyl-N-(2-hydroxyethyl)-pyrrolidinium, N,N-dimethylmorpholinium, N-methyl-N-(2-hydroxyethyl)-morpholinium, N,N-dimethyl-piperidinium and N-methyl-N-(2-hydroxyethyl)-piperidinium salts, which are characterized by an especially good water-solubility. In principle, however, there can be used all the ammonium salts which are physiologically compatible.

The term "lower alkyl" as used herein contemplates straight chain hydrocarbon radicals containing from one to three carbon atoms and includes methyl, ethyl and propyl.

The compounds of formula 1 in which Z is $C(CH_3)OH$ or CHOH and $R^1$ and $R^2$ are each hydrogen or methyl are described in the co-pending patent application of Abraham, et al., Ser. No. 351,381, filed Apr. 16, 1973 and entitled "Alkyl Derivatives of Prostanoic Acids and Preparation Thereof."

The compounds of formula 1 in which Z is $CH_2$ and $R^4$ is hydrogen or methyl are described by C.J. Sih et al., Tetrahedron Letters, 2435 (1972). Esters other than methyl are readily prepared from the latter acid by known methods.

The compounds of formula 1 in which Z is C=O and CHOH, $R^1$ and $R^2$ each are hydrogen and $R^3$ is $(CH_2)_3CH_3$ are described in several publications, for example see Dutch Pat. No. 7,208,955, published Jan. 2, 1973.

The compounds of formula 1 in which $R^3$ is cyclohexyl are prepared by subjecting 2-(6-carboxyhexyl)-1-(tetrahydropyran-2-yl)oxycyclopentan-3-al methyl ester, described in Dutch Pat. No. 7,208,955, cited above, to a sequence of reactions described in British Pat. No. 1,218,998, published Jan. 13, 1971. More specifically, the latter compound is treated with (3-cyclohexyl-2-oxopropyl)phosphoric acid dimethyl ester prepared by reacting ethyl cyclohexylacetate with diethyl methylphosphonate according to the procedure of E.J. Corey and G.T. Kwiatkowski, J. Amer. Chem. Soc., 88, 5654 (1966), to obtain trans-2-(4-cyclohexyl-3-oxo-1-butenyl)-5-[(tetrahydropyran-2-yl)oxy]cyclopentaneheptanoic acid methyl ester. The last-named compound is reduced with sodium borohydride to obtain trans-2-(4-cyclohexyl-3-hydroxyl-1-butenyl)-5-[(tetrahydropyran-2-yl)oxy]cyclopentaneheptanoic acid methyl ester, which is converted to its corresponding acetate on treatment with pyridine and acetic anhydride. Treatment of the corresponding acetate with an acid, preferably aqueous acetic acid, gives trans-2-(4-cyclohexyl-3-acetoxy-1-butenyl)-5-hydroxycyclopentaneheptanoic acid methyl ester, which is oxidized with chromic acid in acetone (Jones reagent) to yield trans-2-(4-cyclohexyl-3-acetoxy-1-butenyl)-5-oxocyclopentaneheptanoic acid methyl ester. Treatment of said last-named compound with sodium methoxide or sodium carbonate affords the desired compound of formula 1, trans-2-(4-cyclohexyl-3-hydroxy-1-butenyl)-5-oxocyclopentaneheptanoic acid methyl ester, as a mixture of epimers with respect to the asymmetric carbon atom to which the hydroxyl is attached. If desired, this mixture is separated into its individual epimers by chromatography. Furthermore, if desired, the latter compound, either as a mixture of epimers or as an individual epimer, is converted to its corresponding acid by treatment with aqueous sodium or potassium hydroxide in a lower alkanol.

When the prostaglandin derivatives of formula 1 are employed according to the method of this invention, they are administered alone or in combination with an antiinflammatory agent with or without a pharmaceutical carrier. In the general embodiment of this invention the route of administration of the active ingredients is not crticial. The prostaglandin derivative and the antiinflammatory agent are both capable of being administered perorally or parenterally, simultaneously or separately. The proportions of the prostaglandin derivative and of the antiinflammatory agent, if present, are determined by their solubilities, by the chosen route of administration and by standard biological practice. For many reasons oral administration is preferred. A convenient and practical pharmaceutical composition in solid form entails the prostaglandin derivative, and if desired the antiinflammatory agent, containing such excipients as starch, lactose, sucrose, cellulose, certain types of clay, silica and flavoring and coating agents; see for example, "Remington's Pharmaceutical Sciences," 14th ed., Mack Publishing Co., Easton, Penn., 1970, p. 1649.

Typical therapeutic compositions containing both the prostaglandin derivative and the antiinflammatory agent in solid form comprise mixtures of these derivatives with indomethacin in a 1:10 to 1:1,000 ratio by weight or with phenylbutazone or oxyphenylbutazone in a 1:5 to 1:100 ratio.

Alternatively, the derivatives with or without the antiinflammatory agent are readily made up in the form of sterile solutions, emulsions and suspensions for oral administration. The solutions are prepared according to well known techniques; see for example, "Remington's Pharmaceutical Sciences," cited above, p. 1478. A convenient formulation for the water soluble salts of acid derivatives of formula 1, noted above, is in the form of a sterile aqueous solution containing 1 to 10% by weight of the derivative. Suitable suspending agents for preparing formulations of the mixture of the prostaglandin derivative and the antiinflammatory agent include water soluble gums, for example, gum arabic, gum tragacanth and other pharmaceutically acceptable suspending or dispersing agent, for example, pectin, sodium alginate, alginic acid, acacia mucilage, carboxypolymethylene, sodium carboxymethyl cellulose, agar, bentonite, cetyl alcohol, gelatin, methyl cellulose, polyvinyl alcohol, polyvinylpyrrolidone, propylene glycol monostearate, sodium lauryl sulfate, sorbitan monooleate, stearyl alcohol, carrageenin, malt extract, oleyl alcohol, quillaja, tragacanth mucilage and the like.

Typical therapeutic composition in the form of sterile solutions, emulsions and suspensions comprise a mixture of the prostaglandin derivative of this invention with indomethacin in 1:10 to 1:1,000 ratio by weight and the active ingredients constituting 2 to 60% by weight of the composition.

The derivatives with or without the antiinflammatory agent may be administered parenterally. For parenteral administration, the derivative (and agent) is dissolved or suspended in liquid carriers such as distilled water or oils of synthetic, animal, petroleum or vegetable origin, for example, soybean oil, sesame oil, mineral oil or propylene glycol, see also the suspending agents cited above. The usual preservatives and other ingredients used for pharmaceutical preparations for parenteral dose may also be incorporated. The concentration of the active agent in these preparations for parenteral use in selected to provide a generally useful composition.

In general, the pharmaceutical compositions are most desirably administered at a concentration level that will generally afford effective results without causing any harmful or deleterious side effects. The prostaglandin derivatives are given preferably at a daily dose range of from about 0.1 mcg to 50 mg/kg, although as aforementioned variations will occur. However, a dosage level that is in the range of from about 1.0 mcg to about 10 mg per kilo is most desirably employed in order to achieve effective results. With respect to the prophylactic treatment of this invention, it is to be understood that the prostaglandin derivative may be administered separately to a host receiving therapeutic treatment with an antiinflammatory agent or it may be combined with a therapeutic dose of the antiinflammatory agent and the combination administered in unit dosage form to the host in need of antiinflammatory therapy. Therapeutic doses for indomethacin usually range from about 0.1 to 10 mg/kg/day; for man the recommended peroral dose ranging from 0.5 to 4 mg/kg/day or a daily dose of about 25 to 200 mg. Therapeutic doses for phenylbutazone and oxyphenylbutazone usually range from 1 to 20 mg/kg/day; the recommended peroral dose for man ranging from 2 to 16 mg/kg/day or a daily dose of about 100 to 800 mg.

The gastrointestinal side effect inhibiting property of the compositions of the present invention are demonstrable in standard pharmacological tests. For example, in procedures similar to the in vivo test described by Y. H. Lee et al., cited above, for evaluating the effects of a test compound on indomethacin-induced ulcers in the rat, the compounds of formula 1 are shown to be effective, see Examples 1 and 2.

The relevance of the Lee test to the clincal situation of indomethacin-induced ulcers is supported by the fact that, as N.O. Rothermich, J. Amer. Med. Assoc., 195, 531 (1966) found a correlation between indomethacin dosage and the occurence of ulcers in man, Lee found a similar correlation in the rat.

Furthermore, the unexpected advantage of the compounds and combinations of this invention in that they do not cause diarrhea at therapeutic doses is demonstrated readily in an in vivo test in which the compound or combination is given perorally in 0.2% sodium carboxymethylcellulose in water to female mice or rats, the appearance or absence of diarrhea being recorded 60 minutes later.

In this latter test the compounds of this invention, for example 2-(3-hydroxy-3-methyloctyl)-5-oxocyclopentaneheptanoic acid or its corresponding (+)- or (−)-enantiomorph, do not cause an appreciable diarrheal effect in female mice at 240 mg/kg whereas prostaglandin $E_2$ causes diarrhea in 50% of the test animals at 43 mg/kg.

The following examples illustrate further this invention.

EXAMPLE 1

By following the procedure of Lee et al., cited above, for the production of the indomethacin-induced ulcer in rats, the property of the compounds of formula 1 to inhibit such ulcers is readily demonstrable. More specifically: male albino rats (170 – 190 g; Sprague-Dawley strain, Canadian Breeding Laboratories), caged individually, were fasted 24 hr with free access to water until the start of the experiment. Indomethacin was given intraperitoneally. The animals were killed 5 hr later and the ulcer formation in the glandular portion of the stomach determined. The compound of formula 1 was administered perorally immediately after the indomethacin. The percent inhibition of ulcer formation versus the semilogarithm of the dose (mg/kg) was plotted and the dose at which 50% inhibition occurred ($ED_{50}$) was read from the graph.

Analysis of variance and regression study were used in the evaluation of the data.

Indomethacin was administered (0.5 ml) as an aqueous suspension (2 drops of polysorbate 80 per 14 ml of $H_2O$). Polysorbate 80 is a mixture of sorbitol and its anhydrides copolymerized with ethylene oxide. The compounds of formula 1 were given (0.2 ml) in a 0.2% sodium carboxymethyl cellulose aqueous suspension.

The results of such a test for 2-(3-hydroxy-3-methyloctyl)-5-oxocyclopentaneheptanoic acid to inhibit the ulcer formation induced by 20 mg/kg i.p. of indomethacin are given in the following table. For comparative purposes the results obtained for propantheline bromide are also included.

| Compound | Dose (mg/kg,p.o.) | No. of Animals | Ulcers Formed Mean ± S.E.M. | % Inhibition | $ED_{50}$ |
|---|---|---|---|---|---|
| None | — | 9 | 10.4 ± 1.3 | — | — |
| 2-(3-hydroxy-3-methyloctyl)-5-oxocyclopentaneheptanoic acid | 0.30 | 9 | 3.2 ± 0.5*** | 69 | 0.11 |
| | 0.15 | 9 | 4.6 ± 0.6** | 56 | — |
| | 0.075 | 9 | 5.9 ± 0.8** | 43 | — |
| propantheline bromide | 6.0 | 8 | 4.1 ± 0.9** | 61 | 3.0 |
| | 3.0 | 9 | 5.0 ± 1.0** | 52 | — |
| | 1.5 | 9 | 6.9 ± 0.9* | 36 | — |

*** $P < 0.001$,
** $< 0.01$,
* $< 0.05$

The results show that 2-(3-hydroxy-3-methyloctyl)-5-oxocyclopentaneheptanoic acid decreased the number of indomethacin-induced ulcers, exhibiting an $ED_{50}$ of 0.11 mg/kg, p.o. over a period of five hours. By comparison propantheline bromide under the same conditions was 27 times less potent having an $ED_{50}$ of 3.0 mg/kg, p.o.

EXAMPLE 2

By following the procedure of Example 1 the effects of compounds of formula 1 other than 2-(3-hydroxy-3-methyloctyl)-5-oxocyclopentaneheptanoic acid on indomethacin-induced ulcers are demonstrable. Accordingly, the results obtained with such other compounds of formula 1 are exemplified by the following list in which the relative potency of each compound with respect to 2-(3-hydroxy-3-methyloctyl)-5-oxocyclopentaneheptanoic acid is noted.

| Compound | Relative Potency ± S.E.M. |
|---|---|
| (−)-2-(3-Hydroxy-3-methyloctyl)-5-oxocyclopentaneheptanoic acid | 1.01 ± 0.40 |
| (+)-2-(3-Hydroxy-3-methyloctyl)-5-oxocyclopentaneheptanoic acid | 1.02 ± 0.42 |
| trans-2-(3-Hydroxyoctyl)-5-oxocyclopentaneheptanoic acid | 0.45 ± 0.12 |
| trans-2-(3-Hydroxyoctyl)-5-oxocyclopentaneheptanoic acid | 0.64 ± 0.20 |
| trans-2-(3-Methyl-3-oxooctyl)-5-oxocyclopentaneheptanoic acid | 0.43 ± 0.14 |
| trans-2-(3-Hydroxy-3-methyl-1-octenyl)-5-oxocyclopentaneheptanoic acid | 1.07 ± 0.33 |
| trans-2-(3-Hydroxy-1-octenyl)-5-oxocyclopentaneheptanoic acid | 0.74 ± 0.20 |
| trans-2-(4-Cyclohexyl-3-hydroxy-1-butenyl)-5-oxocyclopentaneheptanoic acid | 0.13 ± 0.06 |
| trans,cis-7-[2-(3-Hydroxy-1-octenyl)-5-oxocyclopentyl]-5-heptenoic acid (Isomer A)* | 0.37 ± 0.21 |
| trans,cis-7-[2-(3-Hydroxy-1-octenyl)-5-oxocyclopentyl]-5-heptenoic acid (Isomer B) | 0.37 ± 0.14 |
| trans,cis-7-[2-(3-Hydroxy-4,4-dimethyl-1-octenyl)-5-oxocyclopentyl]-5-heptenoic acid | 4.8 |

*This compound is epimeric with the following compound with respect to the asymmetric carbon atom in the side chain bearing the hydroxyl group. It is distinguished from the following compound by being less polar on silica gel thin layer chromatography plates and is arbitrarily designated isomer A. The following compound is then designated isomer B. These compounds are described in Dutch Patent No. 7,208,955, cited above.

EXAMPLE 3

A comparison of the $ED_{50}$ for inhibiting indomethacin-induced ulcers and the $ED_{50}$ for inhibiting gastric acid secretion for compounds of formula 1 is exemplified in the following list. Both $ED_{50}$'s are determined in the rat. The $ED_{50}$ for inhibiting indomethacin-induced ulcers is obtained according to the method of Example 1. The $ED_{50}$ for inhibiting gastric acid secretion is obtained according to the method of Lippmann, cited above.

| Compound | $ED_{50}$ for inhibiting indomethacin-induced ulcer | $Ed_{50}$ for inhibiting gastric acid secretion |
|---|---|---|
| 2-(3-hydroxy-3-methyloctyl)-5-oxocyclopentaneheptanoic acid | 0.11 | 4.3 |
| (+)-2-(3-hydroxy-3-methyloctyl)-5-oxocyclopentaneheptanoic acid | 0.11 | 5.2 |
| (−)-2-(3-hydroxy-3-methyloctyl)-5-oxocyclopentaneheptanoic acid | 0.11 | ca. 12 |
| trans,cis-7-[2-(3-hydroxy-4,4-dimethyl-1-octenyl)-5-oxocyclopentyl]-5-heptenoic acid | ca. 0.02 | ca. 1.0 |

EXAMPLE 4

The inhibitory efect of the compounds of formula 1 on the formation of phenylbutazone-induced ulcers in rats is demonstrable by the method exemplified herein by the choice of 2-(3-hydroxy-3-methyloctyl)-5-ococyclopentaneheptanoic acid as the compound of formula 1.

Male albino rats (140 – 150 g; Sprague - Dawley strain, Canadian Breeding Laboratories), caged individually were fasted 24 hours with free access to water until the start of the experiment. 2-(3-Hydroxy-3-methyloctyl)-5-oxocyclopentaneheptanoic acid was given orally in a suspension of 0.2 ml of 0.2% sodium carboxymethylcellulose in water. Thirty minutes later phenylbutazone (300 mg/kg) in 0.4 ml of an aqueous suspension (1 drop of polysorbate 80 per 14 ml of $H_2O$) was given orally. The animals were killed 18 hours later and the ulcer formation (i.e. number of ulcers) in the glandular portion of the stomach determined. The percent inhibition of ulcer formation versus the semilogarithm of the dose (mg/kg) was plotted and the dose at which 50% inhibition occurred ($ED_{50}$) was read from the graph.

The results of a test according to the preceding method is summarized in the following table.

| Test Compound | Dose mg/kg. p.o. | No. of Animals | Ulcers Formed Mean ± S.E.M. | % Inhibition |
|---|---|---|---|---|
| None | — | 10 | 5.4 ± 1.0 | |
| 2-(3-hydroxy-3-methyloctyl)-5-oxocyclopentane-heptanoic acid | 30 | 9 | 1.2 ± 0.5 | 78 |
| | 15 | 9 | 2.8 ± 0.6 | 48 |
| | 7.5 | 10 | 4.1 ± 1.0 | 24 |

The results show that 2-(3-hydroxy-3-methyloctyl)-5-oxocyclopentaneheptanoic acid decreases the number of phenylbutazone-induced ulcers, exhibiting an $ED_{50}$ of about 15 mg/kg, p.o. over an 18 hr period.

By replacing phenylbutazone with an equivalent amount of oxyphenylbutazone in the procedure of this example, the inhibitory effect of the compounds of formula 1 on the formation of oxyphenylbutazone-induced ulcers in rats is demonstrated.

EXAMPLE 5 a. The following tablet compositions are illustrative of such compositions of this invention:

The prostaglandin derivative, 2-(3-hydroxy-3-methyloctyl)-5-oxocyclopentaneheptanoic acid (2.0 g), is mixed with 196 g. lactose, 44 g microcrystalline cellulose, 4 g stearic acid and 4 g of finely divided silica (Cabosil). The mixture is granulated with addition of a small amount of ethyl alcohol, dried, milled; and compressed into tablets weighing 250 mg each or filled into capsules in amounts of 250 mg each, to make 1,000 tablets or capsules containing 2.0 mg of the active ingredient per tablet or capsule.

In same manner but using 10.0 g of 2-(3-hydroxy-3-methyloctyl)-5-oxocyclopentaneheptanoic acid and 188 g of lactose, together with the same amounts of microcrystalline cellulose, stearic acid and silica as above, 1,000 tablets or capsules containing 10 mg of the active ingredient per tablet or capsule are obtained.

Again in the same manner but adding 25 g of indomethacin and using 0.125 g of the prostaglandin derivative and 172.875 g of lactose together with the same amount of microcrystalline cellulose, stearic acid and silica as above, 1,000 tablets or capsules containing 0.125 mg of the prostaglandin derivative in combination with 25 mg of indomethacin are obtained.

Again in the same manner but adding 40 g of phenylbutazone or oxyphenylbutazone and using 156 g of lactose together with the same amounts of microcrystalline cellulose, stearic acid and silica as above, 1000 tablets or capsules containing 2.0 mg of the prostaglandin derivative in combination with 40 mg of phenylbutazone or oxyphenylbutazone are obtained.

Again in the same manner but addiing 25 g of indomethacin and using 0.40 g of trans,cis-7-[2-(3-hydroxy-4,4-dimethyl-1-octenyl)-5-oxocyclopentyl]-5-heptanoic acid as the prostaglandin derivative and using 172.60 g of lactose together with the same amounts of microcrystalline cellulose, stearic acid and silica as above, 1,000 tablets or capsules containing 0.40 mg of the prostaglandin derivative in combination with 25 mg of indomethacin are obtained.

Again in the same manner, but replacing the above prostaglandin derivative by the same weight of another compound of formula 1, corresponding tablet compositions for the other compounds are obtained.

b. The following liquid compositions are illustrative of such compositions of this invention.

The prostaglandin derivative, 2-(3-hydroxy-3-methyloctyl)-5-oxocyclopentaneheptanoic acid (250 mg), is dissolved in pyrogen-free water (900 ml) by adjusting the pH to 7.5 – 8.5 with sodium hydroxide solution and adding sufficient sodium chloride or sodium citrate or glucose to make the solution isotonic. A preservative such as 0.1 percent weight by volume of methylparaban and 0.015 percent weight by volume of propylparaban or 0.5 percent weight by volume of chlorobutanol is added, the solution is made up to 1,000 ml, sterilized by filtration or autoclaving, and filled into sterile ampoules or vials, to make a solution for parenteral or oral administration containing 0.25 mg of the active ingredient per milliliter.

In the same manner, but using 500 mg of 2-(3-hydroxy-3-methyloctyl)-5-oxocyclopentaneheptanoic acid and proceeding as above but without addition of sodium chloride or citrate or glucose, a solution containing 0.5 mg/ml of the active ingredient is obtained.

Again in the same manner, but using, instead of sodium hydroxide, lithium, potassium, calcium or ammonium hydroxide, or aqueous solutions of methylamine, dimethylamine, trimethylamine, ethylamine, diethylamine, triethylamine, methyl-ethylamine, mono-, di-, or triethanolamine, ethylenediamine, hexamethylenediamine, pyrrolidine, piperidine, morpholine, piperazine, N-methylmorpholine, N-(2-hydroxyethyl)piperidine, or pyridine, or quaternary bases containing the tetramethyl, methyl-triethanol, or trimethylmonoethanol ammonium ion, or the N-methylpyridinium, N-methyl-N-(2-hydroxyethyl)-pyrrolidinium, N,N-dimethylmorpholinium, N-methyl-N-(2-hydroxyethyl)-morpholinium, N,N-dimethylpiperidinium, or N-methyl-N-(2-hydroxyethyl)piperidinium ions, the corresponding salts of 2-(3-hydroxy-3-methyloctyl)-5-oxocyclopentaneheptanoic acid are also obtained.

Again in the same manner but replacing the above prostaglandin derivative by the same weight of another compound of formula 1, corresponding liquid compositions for the other compounds are obtained.

The prostaglandin derivative, trans,cis-7-[2-(3-hydroxy-4,4-dimethyl-1-octenyl)-5-oxocyclopentyl]-5-heptanoic acid (1.0 g) and indomethacin (40.0g) are sterilized separately by autoclaving. Under sterile conditions the latter compounds are mixed with 920 ml of sterile sesame oil and 14 ml of sterile benzyl alcohol, and made up to 1,000 ml with sterile sesame oil. The resulting sterile solution for parenteral administration contains 1.0mg/ml of the prostaglandin derivative and 40.0mg/ml of indomethacin. The suspension is filled into vials under sterile conditions.

c. The following suspension composition is illustrative of such compositions of this invention.

The prostaglandin derivative, trans,cis-7-[2-(3-hydroxy-4,4-dimethyl-1-octenyl)-5-oxocyclopentyl]-5-heptanoic acid (1.0 g) and indomethacin (40.0 g) each are micronized to below 40μ particle size. The two active ingredients are then mixed with 200 ml of water and 140 ml of sugar syrup. Methylparaben (0.625 g) and propylparaben (0.125 g) are dissolved in 100 ml of glycerin with the aid of heat and sodium alginate (25.0 g) is added to the glycerin solution. The glycerin mixture is then added to the above mixture of the active ingredients. The resulting mixture is stirred until an even dispersion is obtained. Flavourings may optionally be added at this point. Thereafter, the suspension is diluted with sufficient water to a volume of 1,000 ml. The resulting suspension for oral administration contains 1.0 mg/ml of the prostaglandin derivative and 40.0 mg/ml of indomethacin.

EXAMPLE 6

3-(Cyclohexyl-2-oxopropyl)phosphoric Acid Dimethyl Ester

Dimethyl methylphosphonate (93 g) is dissolved in tetrahydrofuran (250 ml), cooled to −70°C, and while stirring the mixture with a mechanical stirrer, butyllithium (2.35 molar in hexane; 350 ml) is added at such a rate that the reaction temperature does not increase above −65°C (addition time ~3 hr). Cyclohexylacetyl chloride (40 g) is then added in tetrahydrofuran (30 ml) and again the temperature is not allowed to increase above −65°C during the addition. The mixture is stirred at −70°C for 30 min then allowed to rise to room temperature. The solvent is removed under reduced pressure. The residue is rendered acidic with HCl and dissolved in ether. The ether layer is separated, washed with water, dried and concentrated. The residue is distilled to give the pure title compound, b.p. 138° − 140°C/0.5 mm Hg.

EXAMPLE 7 trans-2-(4-Cyclohexyl-3-oxo-1-butenyl)-5-[(tetrahydropyran-2-yl)-oxy]cyclopentaneheptanoic Acid Methyl Ester To the stirred suspension of sodium hydride (6.32 g; 5% suspension) in dimethoxyethane (400 ml), (3-cyclohexyl-2-oxopropyl)phosphoric acid dimethyl ester (37.3 g), described in Example 6, in dimethoxyethane (300 ml) is added. The stirring is continued for 20 min then 2-(6-carboxyhexyl)-1-(tetrahydropyran-2-yl)oxycyclopentan-3-al methyl ester (34 g), described in Dutch Pat. No. 7,208,955 cited above, is added in dimethoxyethane (400 ml) over a period of 20 min. After 10 min the reaction mixture is rendered neutral with one equiv. of acetic acid and diluted with ether. The ether layer is separated and washed first with saturated NaCl solution and then with water. After drying (MgSO$_4$) the ether layer is concentrated. The residue is subjected to chromatography on 1 kg of silica gel. Elution with ether-hexane (3:7) gives the title compound, $v_{max}^{CHCl_3}$ 1,735, 1,665, 1,620, 1,030 cm$^{-1}$.

EXAMPLE 8 trans-2-(4-Cyclohexyl-3-hydroxy-1-butenyl)-5-[(tetrahydropyran-2-yl)oxy]cyclopentaneheptanoic Acid Methyl Ester Acetate To an ice cold solution of trans-2-(4-cyclohexyl-3-oxo-1-butenyl)-5-[(tetrahydropyran-2-yl)oxy]cyclopentaneheptanoic acid methyl ester (43 g), prepared in Example 7, in 200 ml of methanol, sodium borohydride (3.8 g) is added portionwise. After stirring for 30 min. acetic acid (4.2 ml) is added. The mixture is concentrated under reduced pressure. The residue is taken up in ether. The ether solution is washed to neutral with water and saturated NaCl solution, dried and evaporated to yield trans-2-(4-cyclohexyl-3-hydroxy-1-butenyl)-5-[(tetrahydropyran-2-yl)oxy]cyclopentaneheptanoic acid methyl ester, $v_{max}^{CHCl_3}$ 3,450, 1,735, 1,030 cm$^{-1}$.

The latter compound (40.6 g) is dissolved in pyridine (57 ml). Acetic anhydride (106 ml) is added and the mixture stirred at room temperature for 2 hr. The solution is cooled in ice and the excess anhydride is destroyed by adding carefully some methanol. The solvent is evaporated and the residue taken up in ether. The ether solution is washed with water, dried and the solvent removed to yield the title compound, $v_{max}^{CHCl_3}$ 1,735, 1,240, 1,030 cm$^{-1}$.

EXAMPLE 9 trans-2-(4-Cyclohexyl-3-acetoxy-1-butenyl)-5-oxocyclopentaneheptanoic Acid Methyl Ester trans-2-(4-Cyclohexyl-3-hydroxy-1-butenyl)-5-[(tetrahydropyran-2-yl)oxy]cyclopentaneheptanoic acid methyl ester acetate (44 g), described in Example 8, is dissolved in acetic acid (426 ml), water (212 ml) and tetrahydrofuran (35.7 ml). The mixture is stirred at 60°C (bath temperature) for 3 hr. The solvent is removed under reduced pressure. The residue is taken up in ether. The ether solution is washed with water, dried and evaporated to yield trans-2-(4-cyclohexyl-3-acetoxy-1-butenyl)-5-hydroxycyclopentaneheptanoic acid methyl ester $v_{max}^{CHCl}$ 3,451, 1,730, 1,240 cm$^{-1}$.

To a chilled (−70°C) solution of the latter compound (34.5 g) in acetone (300 ml) a solution of 8N chromic acid (Jones reagent) is added. The addition is stopped when the orange color persists (40 ml). Stirring is continued for 4 more hr. The reaction mixture is allowed to come to room temperature and the solvent removed by distillation under reduced pressure. The residue is taken up in ether. The ether extract is washed with water, dried and evaporated to dryness. The residue is subjected to chromatography on silica gel. Elution with ether-hexane (1:1) yields the title compound, $v_{max}^{CHCl_3}$ 1,735, 1,240 cm$^{-1}$, nmr (CDCl$_3$) δ 2.05 (s,3H), 3.65 (s,3H), 5.4 (m, 1H), 5.55 (m,2H).

EXAMPLE 10 trans-2-(4-Cyclohexyl-3-hydroxy-1-butenyl)-5-oxocyclopentaneheptanoic Acid Methyl Ester To a suspension of trans-2-(4-cyclohexyl-3-acetoxy-1-butenyl)-5-oxocyclopentaneheptanoic acid methyl ester (265 g), prepared as described in Example 9, in methanol (287 ml) is added a solution of sodium methoxide (prepared from 172 g of sodium and 148 ml of methanol). The reaction mixture is stirred at room temperature for 90 min. then rendered neutral with one equivalent of acetic acid. The solvent is evaporated. The residue is taken up in ether. The ether solution is washed with water, dried and the solvent removed to yield the title compound, $\nu_{max}^{CHCl_3}$ 3,450, 1,735 cm$^{-1}$.

The latter compound is a mixture of epimers with respect to the asymmetric carbon to which the hydroxy group is attached. By subjecting the preceding product (22.5 g) to chromatography on silica gel (1 kg) using ether-hexane (1:1) as eluant, the product is separated into its two epimeric forms which are arbitrarily designated Isomer A (less polar isomer) and Isomer B (more polar isomer); the polarity being determined by the order in which these isomers are eluted.

Isomer A: nmr (CDCl$_3$) δ 3.67 (s,3H), 4.26 (m,1H), 5.64 (m,2H).

Isomer B: nmr (CDCl$_3$) δ 3.67 (s,3H), 4.23 (m,1H), 5.62 (m,2H).

EXAMPLE 11 trans-2-(4-Cyclohexyl-3-hydroxy-1-butenyl)-5-oxocyclopentaneheptanoic Acid

To a solution of trans-2-(4-cyclohexyl-3-hydroxy-1-butenyl)-5-oxocyclopentaneheptanoic acid methyl ester, Isomer A (11.56 g), described in Example 10, in 53 ml of methanol is added 10% NaOH (18.3 ml). The mixture is stirred at room temperature for 2 hr then rendered acidic with 10% HCl and diluted with ether. The ether solution is washed with water, dried and evaporated to yield Isomer A of the title compound, $\nu_{max}^{CHCl_3}$ 1730, 1710 cm$^{-1}$.

In the same manner but replacing trans-2-(4-cyclohexyl-3-hydroxy-1-butenyl)-5-oxocyclopentaneheptanoic acid methyl ester, Isomer A, with the corresponding Isomer B, there is obtained Isomer B of the title compound, $\nu_{max}^{CHCl_3}$ 1,730, 1,705 cm$^{-1}$.

EXAMPLE 12

(+)- and (−)-2-(3-Hydroxy-3-methyloctyl)-5-oxocyclopentaneheptanoic Acid

Bioconversion of 2-(3-oxooctyl)-5-oxocyclopentaneheptanoic acid methyl ester, described in U.S. Pat. No. 3,707,548, issued Dec. 26, 1972, with resting cells of *Saccharomyces cerevisiae* (ATCC-4125) gives (+)-2-(3-hydroxyoctyl)-5-oxocyclopentaneheptanoic acid and the optically active enantiomer of the corresponding acid of the starting material, (−)-2-(3-oxooctyl)-5-oxocyclopentaneheptanoic acid. Conversion of the latter acid to its corresponding methyl ester with diazomethane followed by treatment of the ester with methyl magnesium iodide and hydrolysis of the resulting (−)-2-(3-hydroxy-3-methyloctyl)-5-oxocyclopentaneheptanoic acid methyl ester with sodium hydroxide in aqueous methanol gives the desired (−)-enantiomorph, $[\alpha]_D^{25}$ −20.4° (CHCl$_3$).

Esterification of the former compound from the bioconversion with diazomethane and oxidation of the resulting ester with chromic acid in acetone (Jones reagent) gives (+)-2-(3-oxooctyl)-5-oxocyclopentaneheptanoic methyl ester, which on treatment analogous to its above (−)-enantiomorph, i.e. treatment with methyl magnesium iodide followed by hydrolysis, gives the desired (+)-enantiomorph, $[\alpha]_D^{25}$ + 14.3° (CHCl$_3$).

I claim:

1. A method of reducing the incidence of gastrointestinal side effects in a mammal during the treatment of inflammatory conditions with an antiinflammatory agent, which comprises administering to said mammal a gastrointestinal side effect inhibiting amount within the range of about 1.0 microgram to about 10 milligrams per kilogram of trans, cis-7-[2-(3-hydroxy-4,4-dimethyl-1-octenyl)-5-oxocyclopentyl]-5-heptenoic acid during said treatment.

2. A pharmaceutical composition in unit dosage form for treating inflammatory conditions comprising a combination of a gastrointestinal side effect-inhibiting dose within the range of about 1.0 microgram to about 10 milligrams per kilogram of trans, cis-7-[2-(3-hydroxy-4,4-dimethyl-1-octenyl)-5-oxocyclopentyl]-5-heptenoic acid and a therapeutic dose of an antiinflammatory agent.

* * * * *